United States Patent [19]

Sakai

[11] Patent Number: 4,835,262

[45] Date of Patent: May 30, 1989

[54] PROCESS FOR PREPARING PECTIN

[76] Inventor: Takuo Sakai, 13-6, Harayamadai 4-cho, Sakai-shi, Osaka, Japan

[21] Appl. No.: 160,644

[22] Filed: Feb. 26, 1988

[30] Foreign Application Priority Data

Feb. 28, 1987 [JP] Japan .................................. 62-46605

[51] Int. Cl.$^4$ ......................... C08B 37/06; C12N 9/54; C12N 9/56; C12R 1/07
[52] U.S. Cl. ........................................ 536/2; 435/221; 435/222; 435/832; 435/834; 435/835; 435/836; 435/839
[58] Field of Search ..................... 536/2; 435/219, 221, 435/222, 832, 834, 835, 836, 839

[56] References Cited

U.S. PATENT DOCUMENTS 4,686,187  8/1987  Sakai et al. .......................... 435/911

Primary Examiner—John Kight
Assistant Examiner—Mathan M. Nutter
Attorney, Agent, or Firm—Bryan, Cave, McPheeters & McRoberts

[57] ABSTRACT

A process for preparing pectin which comprises subjecting a plant tissue containing pectic substances to the action of a microorganism which belongs to the genus Bacillus and possesses an activity liberating pectin from a plant tissue but substantially does not possess an activity of decomposing pectin, or a culture broth or processed material thereof to liberate pectin from said plant tissue and recovering the pectin, which allows to obtain readily a pectin of high molecular weight in high yield.

5 Claims, 1 Drawing Sheet

PROCESS FOR PREPARING PECTIN

BACKGROUND OF THE INVENTION

1. Field of the Invention

The present invention relates to a method for the isolation of pectin from a plant containing pectin as a constituent, with the use of a microorganism belonging to the genus Bacillus. Pectin is an industrially useful polysaccharide utilized as a raw material for foods, medicines or cosmetics, which is contained in the higher plants in large amounts.

2. Description of the Prior Art

Hitherto, the production of pectin has been carried out by heat-extracting a plant tissue containing pectin as its constituent in the presence of a chelating agent, an acid or the like. However, such method caused difficulty in the isolation of pectin and involved various problems also in the apparatus used in the treatment of residues.

To solve the above problems, microorganisms which produced an enzyme having an activity of liberating pectin from plant tissues containing pectin as their constituent were found, and processes for liberating pectin by subjecting the above-mentioned plant tissues to the action of such microorganisms or of a culture broth or processed material thereof, and recovering the pectin have been proposed (U.S. Pat. No. 4686187 and Japanese Patent Publication No. 46157/1980). However, protopectinases, the pectin-liberating enzymes produced by the microorganisms used in these processes, were all an enzyme which not only liberated pectin from the plant tissues, but also caused a limited decomposition of the pectin once liberated (cf. A Japanese journal "Fermentation & Industries" Vol. 37/1979, pages 928-938). That is, they had an activity of decomposing the liberated pectin (polygalacturonase activity) as well as an activity of liberating pectin (protopectinase activity). Thus, there were problems that decomposition of the liberated pectin took place in parallel with liberating of pectin and so the quality of the pectin obtained was deteriorated due to the decomposition when the enzyme reaction was carried out to the full in order to elevate the yield of pectin.

SUMMARY OF THE INVENTION

The inventor of the present invention has, as the result of keen investigations which were made to solve the above-mentioned problems, found a group of microorganisms producing an enzyme which acts on a plant containing pectin as a constituent and liberates the pectin, but does not decompose the liberated pectin substantially, and reached the present invention. Thus, the present invention provides a process for preparing pectin which comprises subjecting a plant tissue containing pectic substances as its constituent to the action of a microorganism which belongs to the genus Bacillus and possesses an activity of liberating pectin from a plant tissue, but does not substantially possess an activity of decomposing pectin, or a culture broth or processed material thereof, to liberate pectin from the plant tissue, and recovering the pectin.

According to the present invention, pectins having a high molecular weight can be obtained from plant tissues containing pectin as their constituent, in a simple way and a good yield.

DETAILED DESCRIPTION OF THE INVENTION

Figure 1:
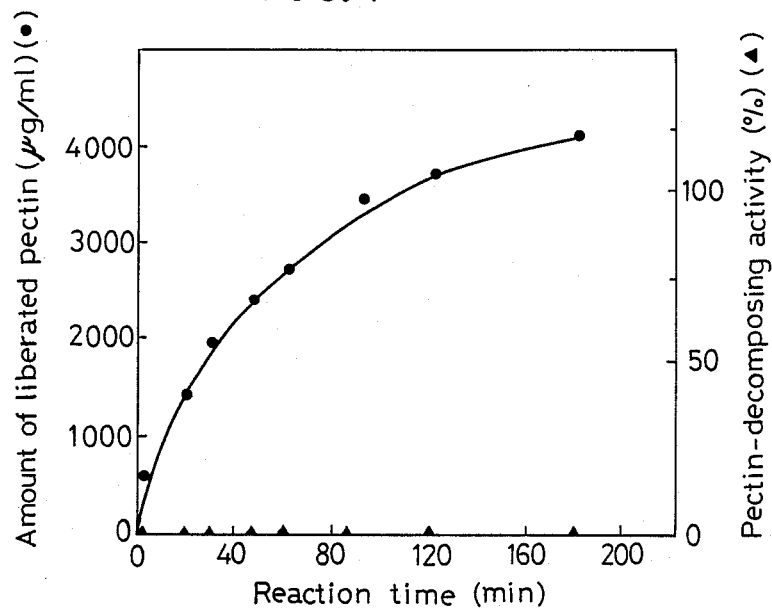
FIG. 1 is a graph showing the time course of the amount of pectin liberated and the pectin-decomposing activity, as protopectin and pectin are subjected to the action of a culture supernatant containing protopectinase of an example of the present invention.

The microorganisms used in the present invention belong to the genus Bacillus. Examples thereof are as follows: *Bacillus subtilis, Bacillus amyloliquefaciens, Bacillus cereus, Bacillus circulans, Bacillus coagulans, Bacillus firmus, Bacillus licheniformis, Bacillus pumilus, Bacillus macerans,* and strains similar to these strains and mutants thereof.

The term "strains similar to these strains" mentioned above means those which possess a pectin-liberating activity, but substantially no pectin-decomposing activity, and have bacteriological properties similar to those of these strains. The term "mutants thereof" includes any of the mutants of the specifically exemplified strains and strains similar thereto which are artificially induced by chemical or physical means or are spontaneously induced. Artificial means which may be used for the mutation are those known in the art.

Further, microorganisms belonging to the genus Bacillus, which produce an enzyme liberating pectin but substantially not decomposing pectin, are included in the present invention insofar as they produce such enzyme, even if they were new strains.

As preferable microorganisms used in the present invention, the following microorganisms all deposited with Institute for Fermentation, Osaka, are mentioned (Figures under IFO denote the deposit number):

(1) *Bacillus subtilis* IFO 3108, 3134, 3336, 3513, 12112, 12113, 12210, 13719, 13721, 14117 and 14140
(2) *Bacillus amyloliquefaciens* IFO 14141
(3) *Bacillus cereus* IFO 3002 and 3132
(4) *Bacillus circulans* IFO 13632
(5) *Bacillus coagulans* IFO 12583
(6) *Bacillus firmus* IFO 3330
(7) *Bacillus licheniformis* IFO 14206
(8) *Bacillus pumilus* IFO 12087
(9) *Bacillus macerans* IFO 3490

Among these microorganism, *Bacillus subtilis* IFO 12113 and *Bacillus subtilis* IFO 13719 are especially favorable.

For the isolation of pectin from a plant tissue according to the method of the present invention, the above microorganism may be directly inoculated into a plant tissue to be treated and cultured under static, agitating or shaking conditions in accordance with conventional methods, or a culture broth which is obtained by cultivating the above microorganism or processed material thereof may be brought into contact with the plant tissue.

Media to be used for the cultivation of the microorganism, i.e. the seed cultivation, are not particularly limited and may be any medium which contains the various nutrients normally used in the conventional cultivation of microorganisms of the genus Bacillus.

The usual media may suitably contain peptone, casein hydrolysate, yeast extract and glucose and, if circumstances require, inorganic salts such as phosphates, magnesium salts, potassium salts, etc. Certain kinds of plant tissues may also be used as the seed cultivation medium, without the addition of any nutrients, but after heat sterilization. The peel or segment cover of citrus fruits is an especially advantageous medium.

The cultivation conditions for the microorganisms in the above-mentioned medium, are properly determined to maximize the amount produced of the intended enzyme, usual conditions being 20°–37° C. for 10–50 hours. The cultivation may be performed under shaking, standing or aeration-stirring, or in a solid state. By such cultivation, mycelium is grown and enzymes are produced out of the mycelium. The culture broth may be utilized as such or as a processed material, such as a concentrate or a solution of purified enzyme. The concentrate may be obtained by subjecting the culture broth, which is, if necessary, filtrated, to a treatment under mild conditions, e.g. evaporation at a low temperature and low pressure or concentration by means of an ultrafiltration membrane. The purified enzyme may be obtained from the broth, by filtrating the broth, concentrating the filtrate and subjecting the concentrate to repeated fractional precipitations by the addition of ammmonium sulfate, or by filtrating the broth and subjecting the filtrate to CM-Sephadex column chromatography and Sephadex G-75 gel filtration.

The mechanism involved in the method of the present invention is considered to be one in which an enzyme produced from the above-mentioned microorganism penetrates into a plant tissue, acts on pectic substances, especially water-insoluble protopectin, to form water-soluble pectin and liberates the water-soluble pectin from the plant tissue.

Pectin liberated from plant tissues by the method of the present invention may be isolated in accordance with conventional methods. For example, the solution, treated as mentioned above, is filtrated to remove off residues, and the filtrate is mixed with three times its volume of a water-miscible organic solvent, e.g., ethanol, to precipitate out pectin. The pectin is collected, washed with a solvent similar to the above organic solvent, e.g., ethanol, and dried to give pectin of high purity. Pectin thus obtained has a molecular weight of more than ca. 110,000, irrespective of the kind of microorganism used for the isolation, and is different from that obtained by the conventional chemical methods in that it has a narrow molecular weight distribution and is closely similar to natural pectin. Furthermore, the pectin is suitable for use as food or medicine, since it does not contain contaminating chemical substances. The properties of pectins obtained vary more or less, according to the kind of raw materials used.

Although the present invention relates to a method of obtaining a pectin of high purity in a simple way and a high yield from plant tissues, by utilizing microorganisms of the genus Bacillus, as described above, such characteristic method of the present invention can be utilized also for the removal of pectin from plant tissues or for the production of an extract of a plant containing pectin.

In addition, the plant tissues used in the treatment of the present invention are preferably those available at a low price and having as high a pectin content as possible, although they are not particularly limited thereto. Examples are citrus fruits, such as Citrus unshiu, Citrus natsu-diadai, lemon, grapefruit, navel orange, orange or the like. Any of the peel and the segment cover of these citrus fruits may be used as the raw material. Namely, it is also possible to use the residue resulting from the pressing of citrus fruits for obtaining fruit juice. Such residue is cheap as a matter of course, and the use thereof serves also for the utilization of waste material. Besides the above-mentioned ones, the peel of fruit-bearing vegetables, such as beet pulp, water melon, melons, etc. and the stem of vegetables such as carrot, burdock, radish, etc. is preferable as the raw material.

According to the present invention, the enzyme which is contained in the microorganism allowed to act on a plant tissue containing pectin as its constituent, in the culture broth of such microorganism, or in the processed material of such culture broth, does not decompose pectin substantially, being different from the known pectinliberating enzymes which decompose pectin itself, and accordingly it is possible, by allowing the enzyme to act on the plant tissue to the full, to liberate pectin to the utmost and obtain pectins having a high molecular weight in a high yield.

Next, the present invention is further explained by giving examples. The invention, however, shall not be limited to these examples.

EXAMPLE 1

In a medium (pH 6.5) containing soluble starch 0.5%, defatted soybean powder 5%, $(NH_4)_2PO_4$ 1%, $CaCl_2 \cdot 2H_2O$ 0.01% and yeast extract 0.01%, each of the strains listed in Table 1 was cultivated under shaking, at 37° C. For 40 hours. The supernant obtained by removing mycelium was allowed to react, as the enzyme source, with a protopectin prepared from the peel and segment cover of lemon (according to the method described in Agric. Biol. Chem., Vol. 46/1982, page 667), as the substrate, at 37° C. to liberate pectin, and the protopectinase activity was determined. The results obtained are given in Table. 1.

By the way, the protopectinase activity was determined according to the method described in Agric. Biol. Chem. Vol. 46/1982, page 667, and the activity which liberated the pectin corresponding to $1\mu$ mol of galacturonic acid, per ml in a prescribed reaction time, was defined as 1 unit of protopectinase.

From the results shown in Table 1, it is evident that microorganisms of a wide range, which belong to the genus Bacillus, have a pectin-liberating activity.

TABLE 1

| Protopectinase activities of various microorganisms of the genus Bacillus | | |
|---|---|---|
| | Protopectinase activity (unit/ml) | |
| Strain | Cultivation at 30° C. | Cultivation at 37° C. |
| *Bacillus subtilis* | | |
| IFO 3108 | 0.5 | — |
| IFO 3134 | 3.1 | — |
| IFO 3336 | 1.3 | 2.4 |
| IFO 3513 | 2.8 | — |
| IFO 12112 | 0.4 | 0.2 |
| IFO 12113 | 6.4 | 8.5 |
| IFO 12210 | 4.8 | 5.2 |
| IFO 13719 | 7.2 | — |
| IFO 13721 | 3.4 | — |
| IFO 14117 | 2.6 | 2.0 |
| IFO 14140 | 0.4 | 0.4 |
| *Bacillus amyloliquefaciens* IFO 14141 | 1.0 | 1.2 |
| *Bacillus cereus* | | |
| IFO 3002 | 0.4 | |

TABLE 1-continued

Protopectinase activities of various microorganisms of the genus Bacillus

| Strain | Protopectinase activity (unit/ml) | |
|---|---|---|
| | Cultivation at 30° C. | Cultivation at 37° C. |
| IFO 3132 | 3.0 | — |
| Bacillus circulans IFO 13632 | 0.2 | — |
| Bacillus coagulans IFO 12583 | 0.5 | 2.5 |
| Bacillus firmus IFO 3330 | 3.0 | — |
| Bacillus licheniformis IFO 14206 | 1.2 | 1.0 |
| Bacillus pumilus IFO 12087 | 5.0 | — |
| Bacillus macerans IFO 3490 | 0.4 | 0.2 |

Note:
— denotes that the strain did not grow at that temperature

Next, the above-mentioned supernatant was allowed to act on protopectin and pectin, and the time course was investigated.

(i) Protopectin

An acetate buffer solution (ph 5.0) containing the culture supernatant having a protopectinase activity of 15 units was allowed to react with 1 ml of aqueous solution containing 20 mg of the above-mentioned protopectin at 37° C., and the time course of the amount of pectin liberated was determined as shown in FIG. 1.

(ii) Pectin

An acetate buffer solution (pH 5.0) containing the same supernatant as mentioned in the above (i) was allowed to react with 0.5% aqueous solution of pectin prepared from lemon (a product of Wako Pure Chemical Co., Ltd.) at 37° C., and the time course of the pectin-decomposing activity was determined and shown in FIG. 1. The pectin-decomposing activity was determined according to the method described in Agric. Biol. Chem., Vol. 46/1982, page 667.

From the results shown in FIG. 1, it is evident that the protopectinase contained in the above-mentioned supernatant has a pectin-liberating activity, but it has no pectin-decomposing activity.

Further, it has been confirmed that every protopectinase produced from the microorganisms listed in Table 1 has no pectin-decomposing activity.

EXAMPLE 2

In a medium (pH 6.5) containing soluble starch 0.5%, $(NH_4)_2PO_4$ 1%, $CaCl_2 \cdot 2H_2O$ 0.1% and yeast extract 0.01%, Bacillus subtilis IFO 12113 and Bacillus subtilis IFO 13719 were cultivated at 30° C. for 24 hours, and 100 ml of the culture filtrate was mixed and allowed to react with 2.5 g of dried peel of Citrus unshiu at 60° C. for 24 hours. The supernatant obtained by filtration was mixed with 3 times its volume of ethyl alcohol, and the pectin formed was collected and dried. Yields and properties of the pectin samples thus obtained are shown in Table 2. Pectins having a high molecular weight were obtained in a high yield, by the full reaction at such high temperature as described above.

TABLE 2

Properties of pectin obtained from the peel of Citrus unshiu

| Properties | Strain used | |
|---|---|---|
| | Bacillus subtilis IFO 12113 | Bacillus subtilis IFO 13719 |
| Yield | 250 mg | 245 mg |
| Methoxylated carboxyl group | 65% | 64.3% |
| Galacturonic acid | 75.8 | 73.1 |
| Neutral sugar | 24.2 | 26.9 |
| Relative viscosity* | 1.37 | 1.41 |
| pH (0.5% solution) | 3.4 | 3.4 |
| Molecular weight** | 110000 | 108000 |
| Found values by elementary analysis | C: 40.50 H: 5.83 N: 0.53 | C: 41.31 H: 5.76 N: 0.48 |

*Measured on 1% sodium hexametaphosphate solution containing 0.1% of pectin dissolved therein
**Determined by the method of Smit and Bryant (J. Food Science, Vol. 32/1967, page 197)

EXAMPLE 3

In a medium which is the same culture medium as used in Example 1 but contains dextrin instead of the soluble starch, Bacillus subtilis IFO 12113 was cultivated at 30° C. for 40 hours. The culture filtrate, as an enzyme solution, was added by 40 units to 50 ml of a solution (pH 5.0) containing 1 g of protopectin of various origins as listed in Table 3. The reaction was allowed to proceed at 37° C. for 1 hour. The amounts of pectin liberated thereby are shown in Table 3.

TABLE 3

Activity of protopectinase-B* on various protopectins

| Origin of protopectin (Botanical name of citrus plant) | Pectin released (mg/g of protopectin) | Relative activity** (%) |
|---|---|---|
| Peel of lemon (Citrus limon) | 19.5 | 100 |
| Peel of BUNTAN (C. grandis) | 39.2 | 191 |
| Peel of PONKAN (C. reticulata) | 34.2 | 167 |
| Peel of YUZU (C. junos) | 27.8 | 136 |
| Peel of KARATACHI (C. trifoliata) | 22.2 | 108 |
| Peel of Lime (C. aurantifolia) | 23.0 | 112 |
| Peel of Valencia orange (C. sinensis) | 27.8 | 136 |
| Peel of BUSSHUKAN (C. medica) | 38.9 | 190 |
| Peel of NAGAMIKINKAN (Fortunella margrigata) | 13.2 | 64 |
| Peel of TOUKINKAN (C. microcarpa) | 18.6 | 91 |
| Peel of Satsuma Mandarin Orange (C. unchiu) | 19.0 | 93 |
| Carrot | 13.0 | 63 |
| Burdock (GOBOU) | 23.4 | 114 |
| Radish | 23.4 | 114 |
| Sugar beet | 23.2 | 113 |

*Definition of the term is given hereinafter
**Rate of activity represented by %, as the activity in the case of peel of lemon is set at 100%

EXAMPLE 4

In a medium which is the same culture medium as used in Example 1 but contains peptone 0.5% instead of the ammonium phosphate, Bacillus subtilis IFO 12113 was cultivated at 30° C. for 36 hours. The culture filtrate, as an enzyme solution, was added to 100 ml of a solution (pH 5.0) containing 10 g of protopectin prepared from lemon. The reaction was allowed to proceed at 37° C., and the amount and the molecular weight of pectin liberated were determined periodically. The results are shown in FIG. 2.

Figure 2:
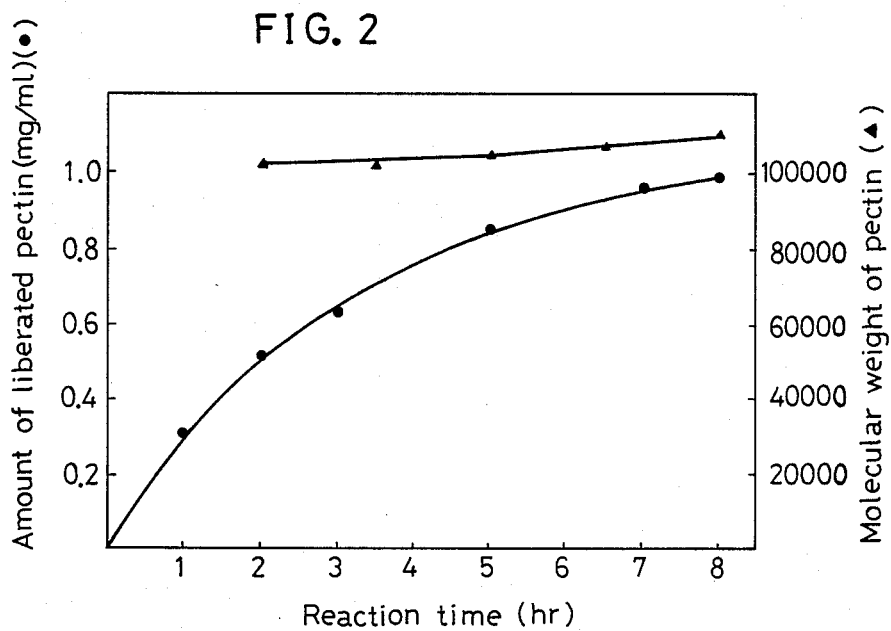
FIG. 2 is a graph showing the time course of the amount of pectin liberated and the molecular weight of pectin liberated, as protopectin is subjected to the action of a culture supernatant containing protopectinase as an example of the present invention.

From the results shown in FIG. 2, it is evident that the liberated pectin is not decomposed.

Next, the protopectinase produced by *Bacillus subtilis* IFO 12113 was purified and its properties were determined.

Method of purification

The strain was cultivated in the medium of Example 1 at 37° C. for 20 hours, and the culture filtrate (20 l) was concentrated to 2 l. The concentrate was dialyzed against 20 mM acetate buffer, and then applied to a CM-Sephadex C-50 column (5×46 cm) equilibrated with the same buffer. The enzyme was eluted with NaCl (0-500 mM) concentration gradients. The enzyme solution was allowed to pass through a DEAE-Toyopearl 650 column (2.1×15 cm), and the solution which passed through the column was collected. Then the solution was concentrated to 4 ml and subjected to chromatography with a Toyopearl HW 55S column (2.5×75 cm). Protopectinase fractions were collected and concentrated, and, after adding powdery ammonium sulfate thereto, allowed to stand in a refrigerator for 1 week, whereby 42 mg of needles was obtained. The enzyme thus obtained is a novel protopectinase, which is named "protopectinase-B".

Properties of the enzyme protopectinase-B are shown in Table 4, and the results of amino acid analysis of the enzyme protopectinase-B are shown in Table 5.

TABLE 4

| Properties of protopectinase-B | |
|---|---|
| Molecular weight (kDa) | |
| By SDS-polyacrylamide gel electrophoresis | 29.0 |
| By Gel filtration | 28.0 |
| By Ultracentrifugation | 28.0 |
| Sedimentation constant ($S_{20}$, w) | s 3.045 |
| Isoelectric point | 9.4 |
| Extinction coefficient (1% aqueous solution, 280 nm) | 15.1 |
| Optimum pH | 7.0–8.0 (37° C.) |
|  | 4.5–5.5 (60° C.) |
| Optimum temperature (° C.) | 37–60° C. |
| Inhibitor | Ba, Ca, Ni |
| Crystal form | needles |

TABLE 5

| Amino acid analysis of protopectinase-B from *Bacillus subtilis* IFO 12113 | | | | | |
|---|---|---|---|---|---|
| Amino acid | mol* | | | | |
| | | Threonine | 14 | Proline | 3–6 |
| Glycine | 22 | Phenylalanine | 5 | Aspartic acid + asparagine | 32–44 |
| Alanine | 14 | Tyrosine | 14 | Glutamic acid | 14 |
| Valine | 10 | Tryptophan | 12 | + glutamine | |
| Leucine | 10 | Cystine | trace | Histidine | 6 |
| Isoleucine | 13 | + cystein | | Arginine | 6 |
| Serine | 23 | Methionine | 1 | Lysine | 13 |
| Sum | 212–227 | (molecular weight of 24000–26000) | | | |

*assuming the protein to be 29 kDa

Methods of determining properties of protopectinase-B and methods of amino acid analysis of protopectinase-B are as follows.

Molecular weight:
SDS-polyacrylamide gel electrophoresis
(Weber & Osborn's method described in J. Biol. Chem., Vol. 244/1969, page 4406, was used.), Gel filtration
(Conditions were the same as those for gel filtration in the purification of enzymes described above. As the standard proteins, cytochrome C. lysozyme, α-chymotrypsinogen A, ovalbumin and bovine serum albumin were used.), Ultracentrifugation
(Yphantis's method described in Biochemistry, Vol. 3/1964, page 297, was used.)

Sedimentation constant
(Enzyme was dissolved in 20 mM acetate buffer of pH 6.0 containing 100 mM NaCl to give an enzyme solution containing 5 mg of the enzyme per ml, and the analysis was effected by centrifugation using a Hitachi model 232 analytical ultracentrifuge at 60000 rpm.)

Isoelectric point
Optimum pH and Optimum temperature were determined according to the method of Example 1.

Amino acid analysis

Purified enzyme (18 mg) was dissolved in 6N-hydrochloric acid and sealed in a tube. Decomposition was effected at 110° C. for 30, 48 and 72 hours, and analysis was effected by means of a Hitachi model LA-5 automatic amino acid analyzer.

The action mechanism of the above-described protopectinase-B on protopectin was investigated and confirmed that the enzyme cleaved glycosidic bonds at the endo site of arabinogalactan prepared from soybean. The other microorganisms used in this invention produced the same kind of enzymes. Immunological homology between protopectinases produced by the microorganisms used in this invention and protopectinase-B were investigated and listed in Table 6. Immunological tests were done using antiserum, prepared in a rabbit to the purified protopectinase-B by the double immuno-diffusion method of Ouchterlony (O. Ouchterlony, Acta Pathol. Microbiol. Scand., Vol. 26, p. 507, 1940). The clude enzymes of *B. coagulans* IFO 12583, *B. licheniformis* IFO 14206 and *B. macerans* IFO 3490 formed precipitates with antiserum of protopectinase-B but these enzymes were not identical with protopectinase-B as judged their precipitation profile, and the others did not make precipitation.

Arabinogalactan degrading activity was done as follows: A reaction mixture, containing 3 ml of 1% arabinogalactan, 1 ml of enzyme solution 0.5 ml of 0.2 M acetic acid/sodium acetate buffer (pH 6.0) was incubated at 37° C. for 30 minutes. The reducing sugar released by the action of protopectinase-B was determined as galactose by the Nelson-Somogyi method (M. Somogyi, J. Biol. Chem., Vol. 195, p. 19, 1952).

TABLE 6

| | Enzyme activity (U/ml) cultivating temperature | | Immunological response | Arabinagalactan degrading activity |
|---|---|---|---|---|
| Strain | 30° C. | 37° C. | | |
| *Bacillus subtilis* | | | | |
| IFO 13719 | — | 9.8 | — | + |
| IFO 13721 | — | 4.2 | — | + |
| *B. amyloliquefaciens* IFO 14141 | — | 0.8 | — | + |
| *B. cereus* IFO 3132 | — | 2.6 | — | + |
| *B. coagulans* | — | 2.5 | +* | + |

TABLE 6-continued

Immunological homology between protopectinases produced from microorganisms used in this invention and protopectinase-B

| Strain | Enzyme activity (U/ml) cultivating temperature 30° C. | 37° C. | Immunological response | Arabinagalactan degrading activity |
|---|---|---|---|---|
| IFO 12583 | | | | |
| B. firmus IFO 3330 | — | 1.2 | — | + |
| B. licheniformis IFO 14206 | — | 2.5 | +** | + |
| B. macerans IFO 3490 | — | 0.1 | +** | + |
| B. pumilus IFO 12087 | 4.1 | — | — | + |
| B. circulans IFO 12632 | — | 0.2 | — | + |

*Two sedimentation lines appear.
**Spur appears.

What is claimed is:

1. A process for preparing pectin comprising:
   (1) exposing pectin containing plant tissue to a microorganism or culture broth from the genus Bacillus or a processed material from said culture broth, the microorganism, broth or processed material being capable of liberating pectin from the plant tissue without substantially decomposing the liberated pectin, and
   (2) recovering the pectin.

2. The process of claim 1 wherein the microorganism used is *Bacillus subtilis, Bacillus amyloliquefaciens, Bacillus cereus, Bacillus circulans, Bacillus coagulans, Bacillus firmus, Bacillus licheniformis, Bacillus pumilus, Bacillus macerans,* strains similar to these strains or mutants thereof.

3. The process of claim 1 wherein the microorganism used is selected from the group which consists of
   (1) *Bacillus subtilis* IFO 3108, 3134, 3336, 3513, 12112, 12113, 12210, 13719, 13721, 14117 and 14140,
   (2) *Bacillus amyloliquefaciens* IFO 14141,
   (3) *Bacillus cereus* IFO 3002 and 3132,
   (4) *Bacillus circulans* IFO 13632,
   (5) *Bacillus coagulans* IFO 12583,
   (6) *Bacillus firmus* IFO 3330,
   (7) *Bacillus lichenifomis* IFO 14206,
   (8) *Bacillus pumilus* IFO 12087, and
   (9) *Bacillus macerans* IFO 3490.

4. The process of claim 1 wherein the microorganism used is *Bacillus subtilis* IFO 12113 or *Bacillus subtilis* IFO 13719.

5. The process of claim 1 wherein the plant tissue is a peel or segment cover from citrus fruits.

* * * * *